United States Patent [19]
Frechet et al.

[11] Patent Number: 5,306,561
[45] Date of Patent: Apr. 26, 1994

[54] PREPARATION OF SURFACE-FUNCTIONAL POLYMER PARTICLES

[75] Inventors: Jean M. J. Frechet, Ithaca, N.Y.; Ken Hosoya, Kyoto, Japan

[73] Assignee: Cornell Research Foundation, Inc., Ithaca, N.Y.

[21] Appl. No.: 841,971

[22] Filed: Feb. 20, 1992

[51] Int. Cl.$^5$ ............................ B32B 5/16; B32B 9/00
[52] U.S. Cl. ........................ 428/402; 428/411.1; 428/414; 428/420; 591/65; 591/57; 591/59; 591/64
[58] Field of Search .................... 428/402, 411.1, 414, 428/420; 121/65, 57, 59, 64, 65

[56] References Cited

U.S. PATENT DOCUMENTS

| | | | |
|---|---|---|---|
| 4,791,063 | 12/1988 | Hou et al. | 524/27 |
| 5,041,464 | 8/1991 | Hoshino et al. | 521/57 |

Primary Examiner—John Kight, III
Assistant Examiner—Duc Truong
Attorney, Agent, or Firm—Bruce F. Jacobs

[57] ABSTRACT

Polymer particles having a hydrophobic core and various surface functional groups, particularly hydrophilic and chiral surface functional groups, are produced by adding a non-emulsified functional polymerizable monomer to the aqueous phase of a dispersion of soluble polymer particles which have previously been swollen with an emulsified-monomer and polymerizing the monomers. Preferably the particles are uniform macroporous beads.

27 Claims, 5 Drawing Sheets

PREPARATION OF SURFACE-FUNCTIONAL POLYMER PARTICLES

This invention resulted from the performance under U.S. National Institutes of Health Grant No. GM-44885-01.

BACKGROUND OF THE INVENTION

Polymer beads are usually produced by free radical suspension polymerization, a well known process developed in 1909. See Hofman et al., Ger. Pat. 250,690 (1909). Porous polymer beads based on, for example, poly(styrene-co-divinylbenzene) are widely used in the synthesis of ion-exchange resins. In addition, significant speciality applications exist for the use of such polymer beads in areas related to separation science. These applications include separation of enantiomers from racemic mixtures, analysis of blood samples, water purification, high-performance liquid chromatography, and the like.

Some of these speciality applications require or would benefit from the use of polymer beads which have unique surface properties. For example, when a conventional column containing hydrophobic polymer beads is used in the analysis of human plasma, the proteins in the blood plasma are denatured on the hydrophobic surface of the beads. This eventually destroys the column through clogging which increases the back pressure to such an extent that the column must often be replaced after only a very short useful lifetime. In contrast, a column packed with polymer beads having a hydrophobic core and a hydrophilic outer layer does not suffer from the same problem because the hydrophilic surface does not react with blood protein so as to cause clogging of the column.

Another speciality application is the separation of enantiomers from racemic mixtures. Such chromatographic separations require the use of beads with a chiral surface layer. These separations are important for the analysis, identification, or preparation of optically active compounds.

Other possible applications for which polymer beads having a hydrophilic or chiral outer surface include catalysis in which it is sometimes desirable to segregate an active component at the surface of a solid catalyst. The selection of a reactive chiral or hydrophilic group and its placement at the surface of a polymer bead could accomplish such an active component segregation. In toner chemistry, it is often desirable to modify the surface chemistry of toner particles which are generally non-porous non-cross-linked polymer particles. Currently this is performed through the use of simple mixtures or coatings of the toner particles with the desired additives.

While some polymer beads with hydrophilic surfaces are available, the processes used to produce such polymer beads are difficult to perform, are limited in the types of monomers and groups which they can introduce, and are in many cases not economical. As regards chiral surface groups, polymer beads having chiral surface functionality and hydrophobic cores and processes for producing such are not known in the prior art. Accordingly, the speciality applications discussed previously, which would benefit from the use of such polymer beads, remain as theoretical applications for polymer beads without suitable polymer beads to perform the operation needed by such.

The production of polymer substrates, particles and/or beads having hydrophilic cores and hydrophilic outer layers or hydrophilic surface functionality is disclosed in a number of publications. For example, U.S. Pat. No. 4,571,390 discloses a porous styrene polymer substrate wherein the surface is rendered hydrophilic by chloromethylating it to introduce methylol groups onto the polymerized substrate. The substrate is disclosed as useful in adsorbing high molecular weight proteins. U.S. Pat. No. 4,898,913 is directed to a process for altering a macroporous crosslinked hydrophobic copolymeric lattice produced by a precipitation polymerization of ester monomers. According to the method described therein, the copolymeric lattice, after formation, must be separated from the mixture in which it is formed, and then, in a separate operation, the surface of the copolymer is rendered hydrophilic either by reaction with an aqueous alkali or by a second polymerization using a hydrophilic acrylate monomer.

European Patent No. 0371258 discloses porous polymer substrates comprising an acrylonitrile polymer or copolymer core with a hydrolized surface layer having post-generated amide surface groups. The porous substrates such as beads are disclosed as being useful in chromatography separation processes. The amide surface groups are produced by adding a peroxide to a polymer suspension and heating for a time sufficient to convert about 15 mole percent of the total surface nitrile groups to amide groups. This process and the resulting product are limited to specific types of surface functional groups.

Another polymer bead material having a hydrophilic surface is disclosed in U.S. Pat. No. 4,882,226. The polymer beads comprise (i) a core material obtained by the addition polymerization of monomers comprising methacrylic acid and (ii) a hydrophilic coating which is covalently bonded to the core as a result of complete or partial conversion of the carboxyl function with a compound containing at least three carbon atoms and an epoxy group. The formation of the covalent bond to create the hydrophilic surface is a multi-step and complex process.

An expensive and complicated process for producing polymer microspheres is taught in U.S. Pat. No. 4,170,685. The process involves the production of microspheres by the use of ionizing radiation. Hydrophilic characteristics are provided by addition of a suitable unsaturated comonomer. See also U.S Pat. No. 4,259,223 which discloses a similar process.

Japanese Patent No. 62046260 discloses still another polymer bead material having a hydrophobic core and a hydrophilic surface layer to which a polyethylene fiber is laminated. The multilayer material is disclosed as being useful in determining components in a blood serum solution.

The prior art processes for forming polymer particles with hydrophobic cores and hydrophilic surface layers are either complicated and uneconomical or limited to a specific surface functionality. Moreover, none of the prior art processes describes a method for introducing a chiral functional group to the surface of hydrophobic polymer beads.

Accordingly, it is one of the objects of the present invention to develop an improved process for introducing hydrophilic or chiral surface functionality on hydrophobic porous polymeric particles.

It is another object of the present invention to produce polymeric particles that have chiral groups on their surface.

It is a further object to manufacture polymeric particles from solid monomers or monomers having a low solubility in the polymerization solvent.

SUMMARY OF THE INVENTION

The present invention is directed to a process for the production of porous polymer particles having specific surface functionality and the particles produced therefrom. The process generally comprises (i) adding a non-emulsified functional monomer which also contains at least one polymerizable group into the aqueous phase of a dispersion of soluble polymer which are insoluble in water and particles which have previously been swollen with an emulsified-monomer, (ii) polymerizing the monomers to form polymer particles which are insoluble, and preferably (iii) extracting the initial soluble polymer particles. The non-emulsified functional monomer contains hydrophilic or chiral groups or precursors thereto. The non-emulsified functional monomer is preferably added prior to the initiation of the polymerization though it may be added shortly thereafter.

Polymer particles produced according to this process generally contain hydrophobic cores with an outer layer composed of the polymerized non-emulsified functional monomer. The process is particularly useful in the production of polymer particles having hydrophilic or chiral group surface layers. The polymer particles formed are generally in the form of beads having a size of from about 2 to 20 μm. The beads are preferably of substantially uniform size and shape although the process is suitable for producing beads of varied sizes and shapes. The beads may have no, little, or a substantial amount of porosity as desired for a particular end use. Preferably the beads are macroporous and have a solvent regain of at least about 0.1 ml/g, preferably at least about 0.5 ml/g, and most preferably at least about 1.0 ml/g. When macroporous products are produced, the macropores often are coated with the polymerized functional monomer while the micropores are generally hydrophobic. The polymer beads are particularly useful in water purification, high-performance liquid chromatography, separation of enantiomers from racemic mixtures, size exclusion chromatography, perfusion chromatography, interaction modes of liquid chromatography, waste water treatment, polymer-supported organic reactions, enzyme immobilization, polymer catalysts, analysis of blood plasma, modification of the surface chemistry of toner particles, and other such applications.

DETAILED DESCRIPTION OF THE PREFERRED EMBODIMENTS

Figure 1:
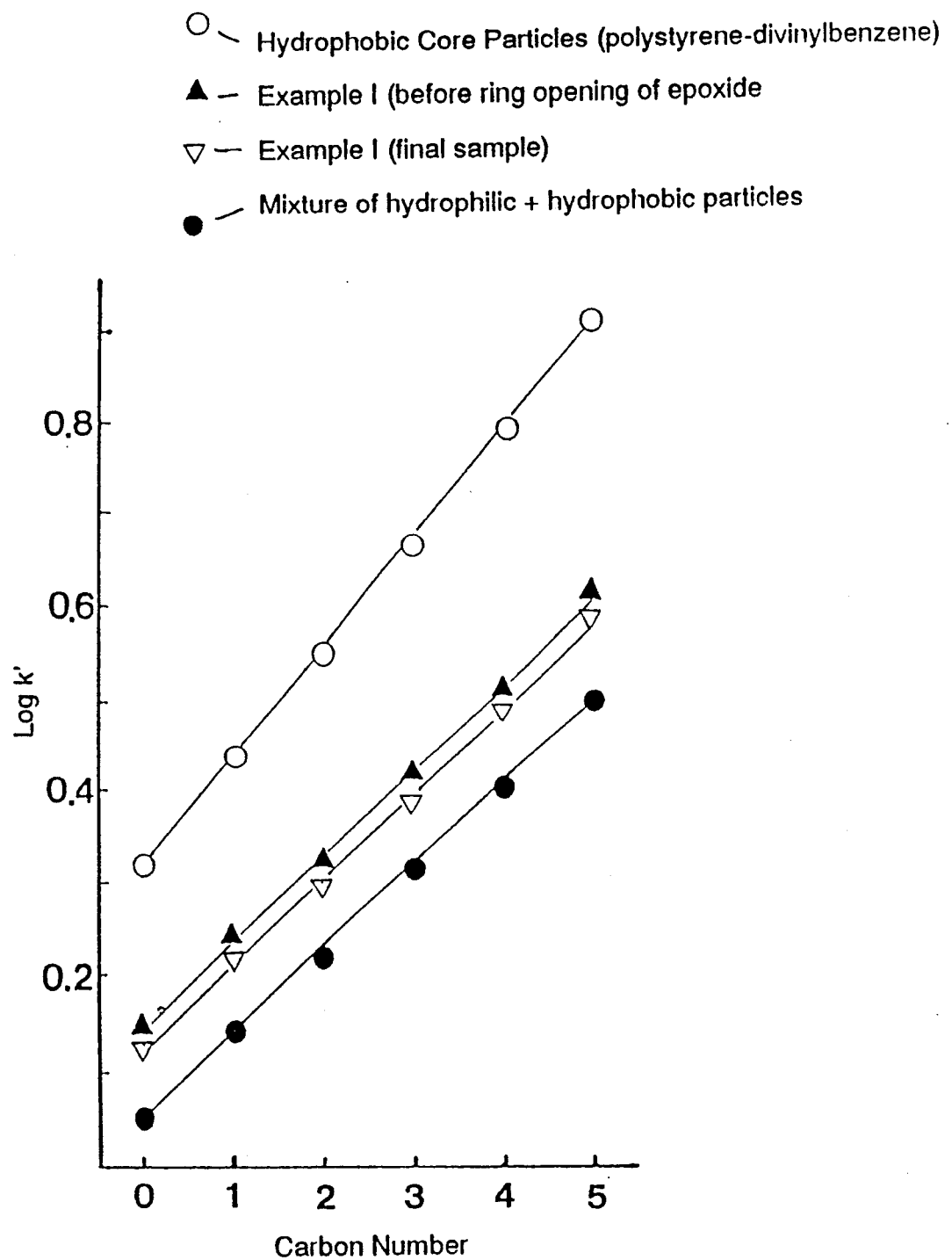
FIG. 1 is a plot of the log k' (capacity factor) of the particles produced in Example I vs. the length of the carbon chain pendant on the benzene rings of the alkylbenzenes used to evaluate the hydrophilicity of the particles produced.

More particularly, the process of the present invention comprises adding a non-emulsified monomer which contains (i) functionality that is hydrophilic or chiral or is a precursor to such functionality and (ii) at least one polymerizable group into the aqueous phase of a dispersion of soluble polymer particles which are insoluble and in water which have previously been swollen with at least one emulsified hydrophobic monomer. The emulsified monomer(s) are then polymerized substantially inside the soluble polymer particles to form a central portion of the new particles and the non-emulsified functional monomer which is in the aqueous phase outside of the soluble polymer particles copolymerizes substantially on the surface of the particles. The inner emulsified monomer and the outer non-emulsified functional monomer surface probably undergo some amount of "mixing" (some of the non-emulsified monomer migrates inside before being polymerized, generally into macropores but not into any micropores) but there is a clear gradient of the composition as one proceeds from the center of the particle to the outside. The new copolymer produced is insoluble. Thereafter, the initial soluble polymer particles may be extracted to produce a porous particle having an outer surface of a polymer of the non-emulsified functional monomer and an inner portion of a hydrophobic polymer. If the initial soluble polymer is not extracted, the resultant particle will still have an outer surface of a polymer of the non-emulsified functional monomer.

Hydrophobic and hydrophilic are relative terms relating to the ability of a material to adsorb or absorb water. For purposes of this invention a material is hydrophilic if it contains at least one water-attracting functional group such as hydroxy, carboxyl, amino, amido, imido, sulfonyl, epoxy, diol, and the like. Materials which are not hydrophilic are hydrophobic for the purposes of this invention. Chiral is used herein to mean an optically active or enantiomerically pure or containing one or more asymmetric center in a welldefined optically active configuration.

The non-emulsified functional monomers which result in hydrophilic surfaces are those monomers which contain a polymerizable vinyl group as well as a hydrophilic group. Suitable such hydrophilic groups include hydroxyl, carboxyl, amino, amido, imido, sulfinyl, sulfonyl, nitro, nitrile, oliol, aminoacid, epoxy, diol, and the like. Accordingly, suitable such monomers include vinyl acetate and other vinyl esters, acrylamide, methacrylamide, hydroxyalkylacrylates and methacrylates such as hydroxyethylmethacrylate, glyceryl acrylate or methacrylate, glycidyl methacrylate, vinyl phenol and esters thereof, acrylic and methacrylic acids and derivatives thereof, vinyl pyridine, vinyl pyrrolidone, aminostyrene, p-epoxystyrene, styrene sulfonic acid and its derivatives, and mixtures thereof. This listing is merely representative of such monomers and not in limitation thereof.

The non-emulsified functional monomers which result in chiral surface functionality are those monomers which contain a polymerizable vinyl group and a reactive chiral group. Suitable such reactive chiral groups include aminoacids, alcohols, amines, esters, amides, sugars, carboxylic acids and esters, and the like. Accordingly, suitable such monomers can be produced by the attachment of known optically active (chiral) compounds to styrenic, acrylic, methacrylic, or other vinylic structure that can be polymerized by conventional free-radical techniques. Generally the attachment will result in pendant chiral groups such as those listed above. This is intended to be merely representative of the chiral monomers and not in limitation thereof.

To achieve the desired result, the non-emulsified functional monomer is one which is not completely water soluble. Rather, it should only be slightly soluble in water. It is preferably added in neat form to the aqueous phase of a previously prepared swollen polymer dispersion. As defined herein, "neat form" means that the monomer is introduced as a pool of liquid or in solid form into the dispersion, and not as part of the emulsified monomer mixture which is used to swell the soluble polymer particles.

The non-emulsified functional monomer is generally added in an amount of from about 1 to 100%, and more preferably in an amount of from about 3 to 30 wt %, based upon the total weight of the soluble polymer and emulsified monomers, though more or less may be used depending upon the thickness and uniformity of the surface layer which is to be produced. Preferably, it is added to the aqueous phase of the swollen soluble polymer particle dispersion prior to initiating polymerization of the emulsified monomer(s), but it may also be added after polymerization has commenced.

When the non-emulsified functional monomer is added prior to the commencement of polymerization, it is desirable to also add a polymerization inhibitor to prevent premature polymerization of it. If such polymerization were to occur, it may reduce the yield of the surface coated particles and also may possibly result in the formation of particles which do not have the hydrophobic central portions. Also when monodisperse soluble polymer particles are used, it could result in the production of particles having different sizes. Suitable inhibitors are known in the art and include, for example, sodium nitrite, ferric chloride, and hydroquinone. The inhibitors are added in an effective amount which is generally of from about 1 to 25 wt % based upon the weight of the initiator.

Initiation is effected in any conventional manner by the introduction of a suitable polymerization initiator such as benzoyl peroxide, lauroyl peroxide, redox initiator systems, or an azo compound such as azobisisobutyronitrile. The initiator is generally present in an amount of from about 1 to 2 wt %, based upon the total weight of the polymerizable monomers present.

The polymerization is carried out in a conventional manner, generally at a temperature of from about 50° to 90° C. for a period of from about 6 to 24 hours, depending upon the initiator and monomers used. Polymerization proceeds rapidly within the confines of the swollen polymer particles to produce a hydrophobic core which is later made porous by extraction of the soluble polymer and any swelling or porogenic solvent. While the polymerization within the particles occurs, the non-emulsified monomer slowly migrates to the surfaces of the polymerizing particles and of the forming macropores where it is copolymerized thereon to form a functionalized hydrophilic or chiral outer surface layer. It is believed that the inner and outer layers of the particles undergo some amount of mixing as some of the non-emulsified monomer migrates further inside the polymerizing particle before undergoing polymerization. This creates a gradient of composition as one proceeds from the outer surface of the particles to the core. This gradient is believed to be rather sharp with the surface functional groups not extending very deeply into the core.

After polymerization is complete, the polymerized dispersion is added to a suitable solvent, such as methanol tetrahydrofurane, benzene, toluene, dioxane, or mixtures thereof, and the starting soluble polymer particles are then extracted therefrom forming a porous final particle. This procedure of extraction in a solvent may be repeated numerous times, preferably about 2 to 5 times, to produce the desired surface functionalized porous polymer particles. Optionally, in the case wherein the surface functional groups are hydrophilic, such as when glycidyl methacrylate is used, the hydrophilicity may be increased such as by opening the glycidyl groups to form diols by acid hydrolysis.

The initial dispersion of swollen polymer particles in water may be formed by a conventional method known in the art. However it is presently preferred to carry out the process as set forth hereinafter to produce macroporous monodisperse particles. A water dispersion containing monodisperse soluble polymer particles, which particles will act as the primary porogen in the process, is formed. The particles then go through a swelling stage, which may be performed in one or more steps, during which the polymer particles solvate. It is presently preferred to carry out the swelling in two steps. First, a solvent usually containing a dissolved free radical initiator is emulsified in water then a dispersion of the polymer particles is added and the polymer particles are allowed to absorb the solvent-initiator emulsion. This solvates the polymer particles and may even dissolve them, changing the particles to solvated droplets. Thereafter, an emulsified monomer or monomer mixture which may also contain a porogenic solvent and a free radical initiator if none was added earlier is added and the swelling (size extension) is completed by absorption of the monomer or monomer mixture by the solvated polymer droplets. In an alternative, the emulsified monomer or monomer mixture may be added first and then followed by the solvent and initiator, or both the solvent and monomer with initiator may be added simultaneously. The monomers and solvents have to be miscible and be capable of solvating the polymer of the primary particles. When particles of a very small size are desired or when only a small enlargement of the size of the primary particle is desired, the addition of the organic solvent may be omitted thus simplifying the process. After absorption of the monomer or mixture of monomers, initiator, and optional solvent into the polymer particles, the dispersion of swollen polymer particles is ready for the introduction of the non-emulsified functional monomer.

The starting soluble polymer particles used in the process of the present invention serve to control the shape and size distribution of the final product. They also serve as a primary component of the porogen. Soluble polymer particles useful herein are insoluble in water but soluble in various organic solvents and include polymers and copolymers containing, for instance, styrene or ring substituted styrenes, acrylates, methacrylates, dienes, vinylchlorides, or vinylacetate. It is presently preferred to employ a polystyrene or an acrylic polymer. The starting polymer particles can be prepared by any technique producing very uniformly sized particles, e.g. by conventional techniques such as emulsion or dispersion polymerizations. The polymer particles initially generally have a diameter of from about 0.5 to 10 μm, more preferably of from about 1 to 6 μm, and most preferably of from about 2 to 5 μm. The initial particle size will, of course, depend upon the intended end use and size of the final particles. For example, to obtain a final bead having a size of about 5 μm, an initial bead size of about 2 μm is recommended. A 5 μm bead is typically used in high-performance liquid chromatography. If uniformity is not desired, the initial bead size is not as important and can, of course, vary resulting in a final product having variable size particles.

The soluble polymer particles must be solvated by the solvent employed in this stage of the process or by the monomer mixture if no solvent is used. The organic component of the emulsified liquid phase is allowed to diffuse or absorb slowly into the polymer particles solvating them and increasing their size in a very uniform manner. Accordingly, the polymer particle size is increased during solvation without any appreciable change in the overall size distribution of the solvated particles. The polymer particles are generally present in the three phase dispersion in an amount of from about 1 to 5% by volume.

In the process of the present invention, the amount of soluble polymer remaining in the polymer particles after polymerization is completed is generally from about 6 to 50 wt %, preferably from about 10 to 30%.

The swelling solvent employed in the present invention contributes to both swelling or solvation of the soluble polymer particles and to the formation of pores during the polymerization reaction. This may be any suitable solvent such as toluene, 1-chlorodecane, 1-bromodecane, dibutylphthalate, chlorobenzene, or mixtures thereof which can solvate the polymer particles used. The solvent is generally present in an amount of from 10 to 80% by volume of the volume of the initial polymer particles, preferably about 10 to 60%.

Suitable monomers which may be used to form the particle core include vinyl monomers or more usually a mixture of vinyl monomers consisting of both a di- or polyvinyl monomer and a monovinyl monomer. Suitable divinyl components include, e.g. divinylbenzene, divinylpyridine, ethylene dimethacrylate, ethylene diacrylate and divinylether. The monovinylic monomers will generally be chosen from the group comprising styrene, ring substituted styrenes, methacrylates, acrylates, conjugated dienes, and the like. The crosslinking monomer is present in the monomer mixture in an amount of from about 10 to 100% by volume. The total amount of monomers present in the three phase dispersion is calculated from the expected particle size taking into account the volume of the inert solvent and the volume of the primary particles themselves.

In addition to the primary components of the three phase dispersion, the dispersion will also generally include both an emulsifier and a suspension stabilizer. Suitable ionogenic or non-ionogenic emulsifiers include such as sodium dodecyl sulfate, alkyl- or dialkyl phenoxypoly(ethyleneoxy) ethanol, and polyoxyethylene sorbitan esters of fatty acids. Suspension stabilizers of the sterical type which may be employed include polymers such as polyvinylalcohol, polyvinylpyrrolidone, polydiethylacrylamide, poly(2-hydroxypropyl methacrylamide), and hydroxypropyl cellulose. The emulsifier is generally present in an amount of from 1 to 5 g/l of the water phase while the concentration of the steric suspension stabilizer generally ranges from 5 to 30 g/l of the water phase.

The process of the present invention will now be described with reference to the following non-limiting examples in which all parts and percents are by weight unless otherwise specified.

EXAMPLE I

Preparation of Soluble Polymer Particles

Monodisperse polystyrene primary particles with a diameter of 1.5 μm were prepared by a standard emulsifier-free emulsion polymerization as follows: in a 1000 ml round bottom reactor containing 700 ml of distilled water in which 0.65 g of sodium chloride was dissolved, 85 g of purified styrene was added. The mixture was flushed with nitrogen gas for 30 min and then heated to 75° C. under stirring (350 rpm) and a nitrogen flushed solution of 0.5 g of potassium persulfate in 65 ml of distilled water was admixed. The polymerization proceeded at 75° C. and 350 rpm for 24 hours. The product was purified from the remaining salts by repeated centrifugation and redispersion by sonication in water until the supernatant was clear. The final dispersion contained 7.2% solids after evaporation. The yield from several different emulsifier-free emulsion polymerization runs ranged from 75 up to 86% based on the amount of styrene monomer.

Preparation of Swollen Soluble Polymer Particles

An emulsified mixture of solvent and initiator was prepared from 1.6 ml of dibutyl phthalate, 0.15 g of benzoyl peroxide, 10 ml of distilled water, and 0.075 g of sodium dodecyl sulfate by sonication using an ultrasonic homogenizer. To the emulsified mixture was added 3.5 ml of the dispersion of monodisperse polystyrene primary particles (7.2 wt %, solid=0.26 g, 1.5 μm in size, Mn=133,400). The mixture was stirred slowly for 5 hours at room temperature.

After the adsorption of the solvent and initiator, to this mixture was added an emulsified mixture of monomers and porogenic solvent prepared from 1.5 ml of styrene, 4.8 ml of commercial divinylbenzene, 12.5 ml of toluene, 50 ml of distilled water, and 36 ml of a 10 wt % solution of poly(vinyl alcohol), (PVA), in water [87–89% hydrolyzed poly(vinyl alcohol) with molecular weight 85,000 to 146,000] by sonication using an ultrasonic homogenizer. The mixture was stirred slowly for 39 hours at room temperature.

Preparation of Glycidyl Methacrylate Coated Particles

To the above prepared swollen particles, 0.005 g of sodium nitrite was added and the dispersion was flushed with nitrogen gas for 20 minutes, then 2 ml of neat glycidyl methacrylate, a hydrophilic monomer which forms a hydrophilic surface layer on the styrene-divinylbenzene crosslinked copolymer core, was added to the reaction vessel. The heterogeneous mixture was heated to 70° C. for 22 hours while stirring slowly to effect polymerization of the emulsified monomers and the nonemulsified glycidyl methacrylate.

The polymerized dispersion was poured into 300 ml of methanol and the supernatant liquid was removed and discarded after sedimentation. The polymer particles were redispersed in 300 ml of tetrahydrofuran then allowed to sediment again and the supernatant liquid was discarded again. This procedure was repeated with 2 portions of tetrahydrofuran. Since the volume ratio of porogenic solvent to monomers was 63:37, the final polymer had approximately 60 vol % porosity. The final macroporous particles were essentially monodisperse with a size of 5 5 μm while the yield was 85% based on the total weight of monomers.

Ring Opening of Epoxide Group

In order to increase the hydrophilicity of the polymerized glycidyl methacrylate surface, the epoxy rings of the glycidyl groups were opened to diol groups by acid hydrolysis as follows: 4.02 g of the macroporous particles were treated with 20 ml of 0.1 M $H_2SO_4$ aqueous solution at 80° C. for 4 hours with intermittent shaking, then the polymer particles were washed with water, followed by 50% aqueous methanol, methanol, and acetone and dried. A quantitative yield of macroporous polymer particles with a size of 5.5 μm were recovered.

Analysis of Particles Formed

To confirm that hydrophobic core particles with a hydrophilic outer layer had been formed, the hydrophobicity and other properties of columns packed with the particles was tested in reversed-phase mode and compared to (i) particles having no hydrophilic outer layer and (ii) simple mixtures of hydrophobic and hydrophilic particles. Chromatographic tests were performed with the separation of a series of small molecules, i.e. alkylbenzenes, the mobile phase selected was 80% aqueous acetonitrile at 1 mL/min.

The test results demonstrate the production of the desired hydrophobic-hydrophilic layer structure as follows:

(1) The particles exhibit a more hydrophilic character than particles having only a hydrophobic composition. In other words, measurements of hydrophobicity showed a lower value for the particles with the hydrophilic surface than for untreated hydrophobic particles. FIG. 1 plots the log k' (the capacity factor) as a function of the length of the carbon chain pendant on the benzene rings of the alkylbenzenes. The higher the slope of the line, the higher the hydrophobicity. As can be seen, the particles having a hydrophobic layer only are the most hydrophobic.

(2) Since the hydrophilic outer layer particles produced also have hydrophobic cores, small molecules such as alkylbenzenes should be retained within the inner pores of the particles. As such, the retention time of the alkylbenzenes should be longer than would be the case if a mere mixture of hydrophobic and hydrophilic particles were present. This is actually observed.

(3) The hydrophilic outer layer particles exhibit water-wettability while both hydrophobic particles and mixtures of hydrophobic and hydrophilic particles are non-water-wettable.

These findings demonstrate that the particles produced have a hydrophilic outer layer and a hydrophobic core.

EXAMPLE II

An emulsified mixture of solvent and initiator was prepared from 1.9 ml of dibutyl phthalate, 0.17 g of benzoyl peroxide, 15 ml of distilled water, and 0.08 g of sodium dodecyl sulfate by sonication using an ultrasonic homogenizer. To this emulsified mixture was added 4.0 ml of the dispersion of monodisperse polystyrene primary particles prepared in Example I (7.2 wt %, solid +0.3 g, 1.5 μm in size, Mn=133,400 Daltons). The mixture was stirred slowly for 23 hours at room temperature. After the adsorption of the solvent and initiator, an emulsified mixture of monomers and porogenic solvent was added. This mixture was prepared from 8.5 ml of divinylbenzene (80%), 9.7 ml of toluene, 50 ml of distilled water, and 40 ml of a 10 wt % solution of poly(vinyl alcohol) in water [PVA ca. 88% hydrolyzed with MW ca. 70,000 to 150,000 Daltons] by sonication using ultrasonic homogenizer. The mixture was stirred slowly for 47 hours at room temperature, then 0.01 g of sodium nitrite was added and the dispersion was flushed with nitrogen gas for 20 minutes. Then 1 ml of ethylene glycol dimethacrylate (neat liquid) was added and the whole heterogeneous mixture was heated to 70° C. for 24 hours while stirring slowly to effect the polymerization.

The polymer particles having hydrophilic groups on their surfaces were recovered as in Example I. The volume ratio of solvents to monomers in the above polymer preparation was 55:45 and thus the final polymer had about 55 vol % porosity. The final macroporous particles were essentially monodisperse with a size of 6.5 μm while the yield was 96% based on the total weight of monomers.

Analysis of Particles Formed

Figure 2:
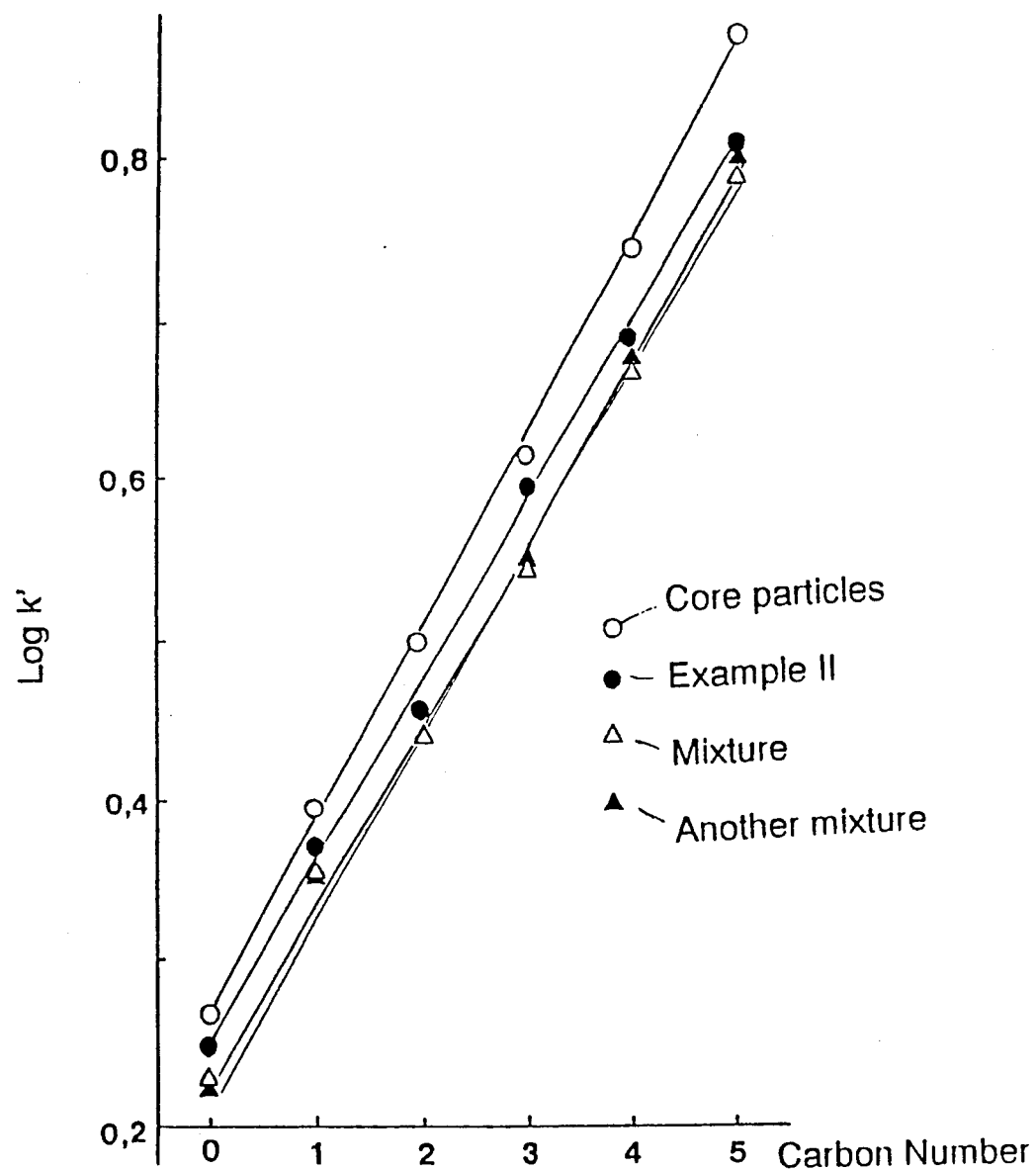
FIG. 2 is a plot of the log k' (capacity factor) of the particles produced in Example II vs. the length of the carbon chain pendant on the benzene rings of the alkylbenzenes used to evaluate the hydrophilicity of the particles produced.

The particles were evaluated as in Example I. Although the monomer utilized to form the outer layer is not very hydrophilic, it exhibits the same relative benefits as in Example I. FIG. 2 is a plot of the log k' as a function of the length of the carbon chain pendant on the benzene rings of the alkylbenzenes. As can be seen, the particles having a hydrophobic-only composition are the most hydrophobic.

EXAMPLE III

An emulsified mixture of solvent and initiator was prepared from 1.9 ml of dibutyl phthalate, 0.17 g of benzoyl peroxide, 15 ml of distilled water, and 0.08 g of sodium dodecyl sulfate by sonication using an ultrasonic homogenizer. To this emulsified mixture was added 5.8 ml of the dispersion of monodisperse polystyrene primary particles prepared by a method similar to that of Example I (5.0 wt %, solid=0.3 g, 1.2 μm in size). The mixture was stirred slowly for 24 hours at room temperature. To this mixture was added an emulsified mixture of monomers and porogenic solvent prepared from 9.2 ml of divinylbenzene (80%), 9.7 ml of toluene, 50 ml of distilled water, and 40 ml of a 10 weight % solution of poly(vinyl alcohol) in water [PVA ca. 88% hydrolyzed with MW ca. 70,000 to 150,000 Daltons]0 by sonication using an ultrasonic homogenizer. The mixture was stirred slowly for 46 hours at room temperature. Then 0.01 g of sodium nitrite was added and the dispersion was flushed with nitrogen gas for 20 minutes. Then 0.48 g of finely powdered solid (S)-N-methacryloyl-α-methylbenzylamine was added and finally the whole heterogeneous mixture was heated to 70° C. for 10 hours while stirring slowly to effect the polymerization.

The polymer particles having chiral groups on their surfaces were recovered as in Example I. Since the volume ratio of solvents to monomers was 52:48, the final polymer had about 50% porosity. The final macroporous particles were essentially monodisperse with a size of 4.4 μm while the yield is 89% based on the total weight of monomers.

Analysis of Particles Formed

Figure 3:
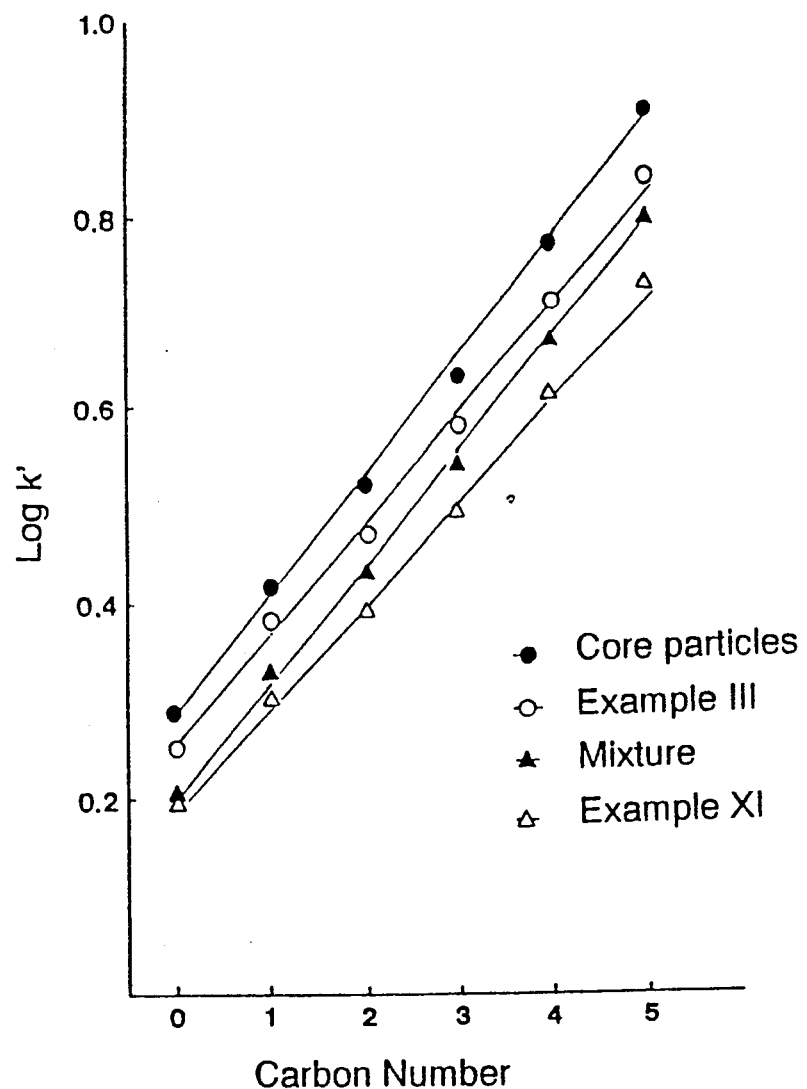
FIG. 3 is a plot of the log k' (capacity factor) of the particles produced in Example III vs. the length of the carbon chain pendant on the benzene rings of the alkylbenzenes used to evaluate the hydrophilicity of the particles produced.
Figure 4:
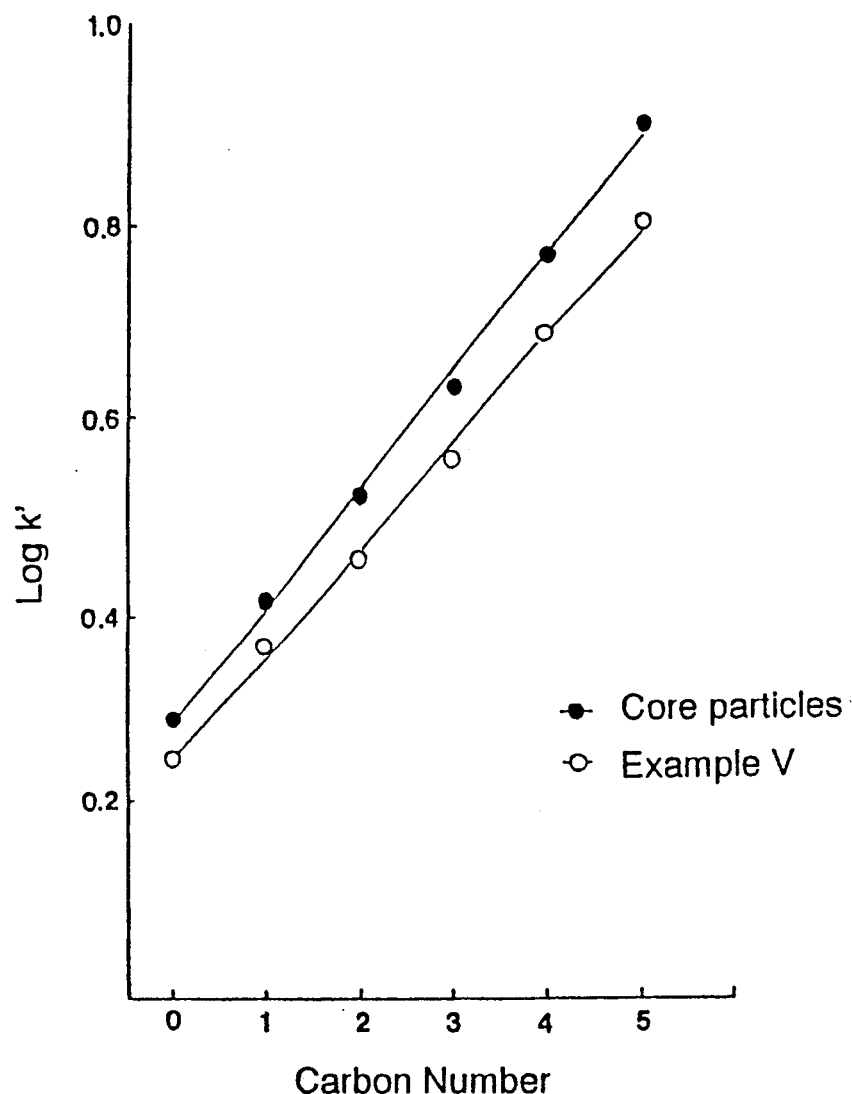
FIG. 4 is a plot of the log k' (capacity factor) of the particles produced in Example V vs. the length of the carbon chain pendant on the benzene rings of the alkylbenzenes used to evaluate the hydrophilicity of the particles produced.

The particles were evaluated as in Example I and the results of the hydrophobicity are shown in FIG. 3. In this case, the monomer used to form the outer layer, (S)-N-methacryloyl-α-methylbenzylamine, also contains a relatively hydrophobic phenyl group. Accordingly, the differences in the graphs are still evident, but less pronounced. This is however necessary for chiral separations due to the occurrence of pi-pi interactions.

EXAMPLE IV

An emulsified mixture of solvent and initiator was prepared from 1.9 ml of dibutyl phthalate, 0.17 g of benzoyl peroxide, 15 ml distilled water, and 0.08 g of sodium dodecyl sulfate by sonication using an altrasonic homogenizer. To this emulsified mixture was added 5.8 ml of the dispersion of monodisperse polystyrene primary particles (5.0 wt %, solid=0.3 g, 1.2 μm in size). The mixture was stirred slowly for 24 hours at room temperature.

After the adsorption of the solvent and initiator, to this mixture was added an emulsified mixture of monomers and porogenic solvent prepared from 9.2 ml of ethylene glycol dimethacylate, 9.7 ml of toluene, 50 ml of distilled water, and 40 ml of a 10 wt % solution of poly(vinyl alcohol) in water (PVA ca. 88% hydrolyzed with MW ca. 70,000 to 150,000 Daltons) by sonication using ultrasonic homogenizer. The mixture was stirred slowly for 46 hours at room temperature, then 0.01 g of sodium nitrite was added and the dispersion was flushed with nitrogen gas for 20 minutes. Then 0.48 g of finely powdered solid (S)-N-methacryloyl--methylbenzylamine was added and the heterogeneous mixture was heated to 70° C. for 23 hours while stirring slowly to effect polymerization.

The polymer particles having chiral groups on their surfaces were recovered as in Example I. Since the volume ratio of solvents to monomers was 52:48, the final polymer had about 50 vol % porosity. The final macroporous particles were essentially monodisperse with a size of 4.4 μm while the yield was 98.6% based on the weight of monomers.

EXAMPLE V

An emulsified mixture of solvent and initiator was prepared from 1.9 ml of dibutyl phthalate, 0.17 g of benzoyl peroxide, 15 ml distilled water, and 0.08 g of sodium dodecyl sulfate by sonication using an altrasonic homogenizer. To this emulsified mixture was added 5.8 ml of the dispersion of monodisperse polystyrene primary particles (5.0 wt %, solid=0.3 g, 1.2 μm in size). The mixture was stirred slowly for 24 hours at room temperature.

After the adsorption of the solvent and initiator, to this mixture was added an emulsified mixture of monomers and porogenic solvent prepared from 8 ml of divinylbenzene (80%), 9.7 ml of toluene, 50 ml of distilled water, and 40 ml of a 10 wt % solution of poly(vinyl alcohol) in water [PVA ca. 88% hydrolyzed with MW ca. 70,000 to 150,000 Daltons] by sonication using ultrasonic homogenizer. The mixture was stirred slowly for 46 hours at room temperature. Then 0.01 g of sodium nitrite was added and the dispersion was flushed with nitrogen gas for 20 minutes. Then 1 g of powdered (1R,2S)-2-[N-(4-vinyl)-benzoylamino]-1-phenylpropyl-(4-v and finally the whole heterogeneous mixture was heated to 70° C. for 23 hours while stirring slowly to effect polymerization. The polymerized dispersion was poured into 300 ml of methanol and the supernatant liquid was removed and discarded after sedimentation.

The polymer particles having chiral group surfaces were recovered as in Example I. Since the volume ratio of solvents to monomers was 52:48, the final polymer had approximately 50 vol % porosity. The final macroporous particles were essentially monodisperse with a size of 4.5 μm while the yield is 81% based on the total weight of monomers.

Analysis of Particles Formed

The particles were evaluated as in Example I and demonstrated the same more hydrophilic behavior than the hydrophobic "core-only" particles.

EXAMPLE VI

An emulsified mixture of solvent and initiator was prepared from 1.9 ml of dibutyl phthalate, 0.17 g of benzoyl peroxide, 15 ml distilled water, and 0.08 g of sodium dodecyl sulfate by sonication using an altrasonic homogenizer. To this emulsified mixture was added 5.8 ml of the dispersion of monodisperse polystyrene primary particles prepared in Example III (5.0 wt %, solid=0.3 g, 1.2 μm in size). The mixture was stirred slowly for 24 hours at room temperature.

After the adsorption of the solvent and initiator, to this mixture was added an emulsified mixture of monomers and porogenic solvent prepared from 8 ml of divinylbenzene (80%), 9.7 ml of toluene, 50 ml of distilled water, and 40 ml of a 10 wt % solution of poly(vinyl alcohol) in water [PVA ca. 88% hydrolyzed with MW ca. 70,000 to 150,000 Daltons] by sonication using ultrasonic homogenizer. The mixture was stirred slowly for 46 hours at room temperature. Then 0.01 g of sodium nitrite was added and the dispersion was flushed with nitrogen gas for 20 minutes. Then 1 g of powdered (1R, 2S)-2-(N-methacryloylamino)-1-phenylpropyl methacrylate was added and the heterogeneous mixture was heated to 70° C. for 10 hours while stirring slowly to effect polymerization.

The polymer particles having chiral groups on their surfaces were recovered as in Example I. Since the volume ratio of solvents to monomers was 52:48, the final polymer had about 50 vol % porosity. The final macroporous particles were essentially monodisperse with a size of 4.0 μm while the yield is 95% based on the total weight of monomers.

EXAMPLE VII

An emulsified mixture of solvent and initiator was prepared from 1.9 ml of dibutyl phthalate, 0.17 g of benzoyl peroxide, 15 ml distilled water, and 0.08 g of sodium dodecyl sulfate by sonication using an altrasonic homogenizer. To this emulsified mixture was added 5.8 ml of the dispersion of monodisperse polystyrene primary particles prepared in Example I (5.0 wt %, solid=0.3 g, 1.2 μm in size). The mixture was stirred slowly for 24 hours at room temperature.

After the adsorption of the solvent and initiator, to this mixture was added an emulsified mixture of monomers and porogenic solvent prepared from 8.5 ml of ethylene glycol dimethacylate, 9.7 ml of toluene, 50 ml of distilled water, and 40 ml of a 10 wt % solution of poly(vinyl alcohol) in water [PVA ca. 88% hydrolyzed with MW ca. 70,000 to 150,000 Daltons] by sonication using ultrasonic homogenizer. The mixture was stirred slowly for 46 hours at room temperature. Then 0.01 g of sodium nitrite was added and the dispersion was flushed with nitrogen gas for 20 minutes. Then 1 g of finely powdered (1R,2S)-2-[N-(4-vinyl)-benzoylamino]-1-phenylpropyl-(4-vinyl)-benzoate was added and the heterogeneous mixture was heated to 70° C. for 24 hours while stirring slowly to effect polymerization. The polymerized dispersion was poured into 300 ml of methanol and the supernatant liquid was removed and discarded after sedimentation.

The polymer particles having chiral group surfaces were recovered as in Example I. Since the volume ratio of solvents to monomers was 52:48, the final polymer had about 50 vol % porosity. The final macroporous particles were essentially monodisperse with a size of 4.3 μm while the yield is 98% based on the total weight of monomers.

EXAMPLE VIII

This example is similar to Example V with the exception that a much larger amount of the functional monomer was added as a solid chunk. Also, as the amount of functional monomer was very large (50% of the total monomer content) some acetone was added as the polymerization was initiated to assist in transport of the non-emulsified functional monomer from the solid chunk to the polymerizing droplets.

An emulsified mixture of solvent and initiator was prepared from 1.9 ml of dibutyl phthalate, 0.17 g of benzoyl peroxide, 15 ml distilled water, and 0.08 g of sodium dodecyl sulfate by sonication using an altrasonic homogenizer. To this emulsified mixture was added 5.8 ml of the dispersion of monodisperse polystyrene primary particles prepared in Example I (5.0 wt %, solid=0.3 g, 1.2 μm in size). The mixture was stirred slowly for 24 hours at room temperature.

After the adsorption of the solvent and initiator, to this mixture was added an emulsified mixture of monomers and porogenic solvent prepared from 4.8 ml of divinylbenzene (80%), 9.7 ml of toluene, 50 ml of distilled water, and 40 ml of a 10 wt % solution of poly(vinyl alcohol) in water [PVA ca. 88% hydrolyzed with MW ca. 70,000 to 150,000 Daltons] by sonication using ultrasonic homogenizer. The mixture was stirred slowly for 46 hours at room temperature. Then 0.01 g of sodium nitrite was added and the dispersion was flushed with nitrogen gas for 20 minutes. Then 4.8 g of chunk (1R, 2S)-2-[N-(4-vinyl)-benzoyl-amino]-1-phenylpropyl-(4-vinyl)-benzoate and 5 ml of acetone were added and heated to 70° C. for 24 hours while stirring slowly to effect polymerization. The polymerized dispersion was poured into 300 ml of methanol and the supernatant liquid was removed and discarded after sedimentation.

The polymer particles were recovered as in Example I. Since the volume ratio of solvents to monomers was 52:48, the final polymer had about 50 vol % porosity. The final macroporous particles were essentially monodisperse with a size of 4.5 μm while the yield was 72% based on the weight of monomer.

Analysis of Particles Formed

Examination by optical microscopy visually confirmed that the final particles contained different outer and inner layers (core-shell type). The low yield obtained is due to the fact that incomplete transfer of the large chunk of monomer was achieved. Some unreacted functional monomer was recovered at the end of the process.

EXAMPLE IX

Figure 5:
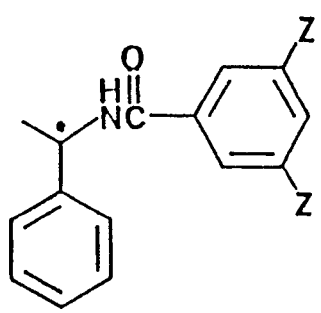
FIG. 5 shows the compounds used in the separation of racemic mixtures in Examples IX and X.

A separation of chiral compounds was performed using a column packed with the material produced as described in Example V. The hplc chromatographic testing was performed in normal phase mode using a non-aqueous organic solvent (n-hexanetetrahydrofuran 4:1 v/v) at 0.5 mL/min with a column 4.6 mm ID X 150 mm long, peak detection was carried out using a UV detector at 254 nm. The solutes were α-methylbenzylamine derivatives in which $\alpha = k'_R/k'_S$, wherein R and S are the two enantiomers being separated. For sample 1 (FIG. 5, Z=H) the α value was determined to be 0.99. For sample 2 (FIG. 5, Z=NO$_2$) the α value was 1.05.

EXAMPLE X

In Example III only 5 wt % of the chiral monomer was used. When the resultant particles were evaluated for chiral recognition, it was determined that they were relatively ineffective. Accordingly, the procedure of Example III was repeated except that the amount of the chiral monomer introduced was increased to 20 wt %, i.e. the amount of divinyl benzene was 7.76 mL and the amount of chiral monomer was 1.94 g. The yield of final particles was 65% due to some loss of material from the outer non-crosslinked layer during the tetrahydrofuran washing. The final particles showed more hydrophilicity than did those particles of Example III.

The resulting particles were evaluated as in Example IX above for chiral separation performance. The results of the two separations afforded α values of 0.94 for each of the samples.

What is claimed is:

1. A process for producing surface functionalized polymer materials comprising (i) adding a non-emulsified functional monomer which further contains at least one polymerizable vinyl group into an aqueous phase of a dispersion of soluble polymer particles which are insoluble in water, soluble in an organic material in the dispersion, and which are swollen with an emulsion of a polymerizable vinyl monomer and (ii) co-polymerizing (a) the emulsified monomer in the swollen particles and (b) the non-emulsified functional monomer, thereby forming an insoluble polymer particle having a hydrophobic polymer core and a functionalized polymer outer layer.

2. The process of claim 1, wherein the non-emulsified functional monomer is added prior to the start of the polymerization.

3. The process of claim 2, wherein a water soluble polymerization inhibitor is added to the aqueous phase of the dispersion prior to the addition of the non-emulsified functional monomer.

4. The process of claim 1, wherein the functional monomer is added neat.

5. The process of claim 1, wherein the non-emulsified functional monomer is a hydrophilic monomer.

6. The process of claim 5, wherein the hydrophilic monomer contains at least one hydrophilic group selected from the group consisting essentially of hydroxyl, carboxyl, amino, amido, imido, sulfinyl, sulfonyl, nitro, nitrile, oliol, aminoacid, epoxy, diol, and mixtures thereof.

7. The process of claim 5, wherein after polymerization is complete the process further comprises increasing the hydrophilicity of the surface of the material produced.

8. The process of claim 1, wherein the non-emulsified functional monomer is a chiral monomer.

9. The process of claim 8, wherein the chiral monomer contains reactive chiral groups suitable to separate racemic mixtures of chiral compounds.

10. The process of claim 8, wherein the chiral monomer contains a polymerizable vinyl group and a pendant reactive chiral group.

11. The process of claim 1, wherein the surface functionalized polymer materials are porous and the process further comprises the step of (iii) extracting the soluble polymer materials.

12. The process of claim 1, wherein the dispersion of swollen soluble polymer particles is formed by dispersing the soluble polymer particles in water and swelling the particles by adding to the dispersion at least one monomer and an initiator for polymerizing the monomer.

13. The process of claim 12, wherein the swelling is performed in two stages, the first stage comprising solvation resulting from absorption by the polymer particles of the at least one monomer and the second stage comprising solvation resulting from absorption by the polymer particles of a solvent.

14. The process of claim 12, wherein the swelling is performed in two stages, the first stage comprising solvation resulting from absorption by the polymer particles of a solvent and the second stage comprising solvation resulting from absorption by the polymer particles of at least one monomer.

15. The process of claim 1, wherein the polymer particles comprise polymers and copolymers of monomers selected from the group consisting of styrene, ring substituted styrenes, acrylates, methacrylates, dienes, vinylchloride, and vinylacetate.

16. The process of claim 12, wherein the at least one monomer is a mixture of vinyl monomers, one of which is a polyvinyl monomer.

17. The process of claim 16, wherein the polyvinyl monomer is selected from the group consisting essentially of divinylbenzene, divinylpyridine, ethylene dimethacrylate, ethylene diacrylate, divinylether, and mixtures thereof.

18. The process of claim 1, wherein the amount of soluble polymer in the particles produced is from about 6 to 50 vol % of the particles.

19. The process of claim 1, wherein the polymer particles employed to start the process have a diameter of from about 0.5 to 10 $\mu$m and the resulting polymer particles have a diameter of from about 2 to 20 $\mu$m.

20. The process of claim 1, wherein the soluble polymer particles remaining after polymerization are substantially extracted using a solvent selected from the group consisting of tetrahydrofurane, benzene, toluene, and dioxan.

21. The process of claim 1, wherein prior to or as part of the preparation of the swollen soluble polymer particles an emulsifier and a suspension stabilizer are also incorporated.

22. A material comprising a polymerized particle having a core comprising a hydrophobic material, said core enclosed by a chiral polymer surface layer.

23. The material of claim 22, wherein the hydrophobic material is composed of polymerized monomers selected from the group consisting of styrene, ring substituted styrenes, acrylates, methacrylates, dienes, vinylchloride and vinylacetate.

24. The material of claim 22, wherein there is a gradient between the center of the core and the outer surface of the chiral polymer layer, whereby the hydrophobic core material decreases in amount as it approaches the outer chiral layer so as to form an intermediate layer containing both chiral polymer and hydrophobic material between the core and the outer chiral polymer layer.

25. The material of claim 22, wherein the chiral polymer surface layer is capable of separating racemic mixtures of chiral compounds.

26. The material of claim 22, wherein the particle is porous.

27. The material of claim 22, wherein the particle is macroporous and has a solvent regain of at least about 0.1 ml/g.

* * * * *